(12) United States Patent
Stahl et al.

(10) Patent No.: US 7,939,118 B2
(45) Date of Patent: May 10, 2011

(54) OLIGOSACCHARIDE MIXTURE

(75) Inventors: Bernd Stahl, Rosbach (DE); Günther Böhm, Echzell (DE); Berndt Finke, Ober-Mörlen (DE); Gilda Georgi, Friedrichsdorf (DE); Jürgen Jelinek, Rosbach (DE); Joachim J. Schmitt, Hösbach (DE)

(73) Assignee: N.V. Nutricia (NL)

( * ) Notice: Subject to any disclaimer, the term of this patent is extended or adjusted under 35 U.S.C. 154(b) by 1231 days.

(21) Appl. No.: 10/148,193

(22) PCT Filed: Dec. 7, 2000

(86) PCT No.: PCT/EP00/12345
§ 371 (c)(1), (2), (4) Date: Aug. 21, 2002

(87) PCT Pub. No.: WO01/42263
PCT Pub. Date: Jun. 14, 2001

(65) Prior Publication Data
US 2003/0129278 A1    Jul. 10, 2003

(30) Foreign Application Priority Data
Dec. 7, 1999 (DE) .................................. 199 58 985

(51) Int. Cl.
*C13K 1/06*    (2006.01)
(52) U.S. Cl. ................ 426/48; 426/658; 127/29; 127/30
(58) Field of Classification Search .................... 426/48, 426/658; 127/29, 30
See application file for complete search history.

(56) References Cited

U.S. PATENT DOCUMENTS
4,944,952 A * 7/1990 Kobayashi et al. ............. 426/42
5,750,176 A * 5/1998 Prieto et al. .................... 426/580

FOREIGN PATENT DOCUMENTS
DE    197 01 382 A    7/1998
EP    0 307 523 A    3/1989
WO    WO 98 43494 A    9/1998

OTHER PUBLICATIONS

Thurl et al., "Quantification of Individual Oligosaccharide Compounds from Human Milk Using High-pH Anion-Exchange Chromatography," Analytical Biochemistry 235, 202-206 (1996).*

* cited by examiner

*Primary Examiner* — Keith D Hendricks
*Assistant Examiner* — Nikki H Dees
(74) *Attorney, Agent, or Firm* — Bacon & Thomas, PLLC

(57) ABSTRACT

An oligosaccharide mixture based on oligosaccharides from one or several animal milks composed of two or more monosaccharide units. The oligosaccharide mixture comprises at least two oligosaccharide fractions which are each composed of at least two different oligosaccharides. Lactose does not pertain thereto and the total spectrum of the oligosaccharides in the oligosaccharide mixture differs from those present in animal milk or animal milks, wherefrom the oligosaccharide fractions are extracted and that a) if the oligosaccharides are extracted from only one animal milk, the proportion of neutral oligosaccharides to acidic oligosaccharides is 90-60:10-40 weight %, or b) if the oligosaccharides are extracted from at least two animal milks, the oligosaccharides extracted from two different animal milks each make up 10 weight % of the total amount of oligosaccharides present in the oligosaccharide mixture. The oligosaccharide mixture approximates human milk with respect to its positive properties.

8 Claims, No Drawings

OLIGOSACCHARIDE MIXTURE

The invention relates to an oligosaccharide mixture of oligosaccharides obtained from one or several animal milks and which are composed of two or more monosaccharide units, and to the use of said oligosaccharide mixture for combating disorders of gastro-intestinal functions.

The concentration of oligosaccharides in mature human milk amounts approximately to 10 g/l. Up to date, about 80 different oligosaccharides present in human milk could be described in their structure, which are composed of 3-13 monomers; Newburg, D. S. and Neubauer, S. H. (1995) Carbohydrates in milk: Analysis, quantities and significance, in: Handbook of Milk Composition, Jensen, R. G., editor. Academic press, 273-349. In the variety of structure of these oligosaccharides, the structural and positional isomerism plays an important role. The relationship of neutral to sialylated (acidic) oligosaccharides or oligosaccharide structures is about 10:1 in mature human milk.

Oligosaccharides play the following important roles in humans for the specific and unspecific defence against infections:

1. Oligosaccharides from human milk constitute a substrate source for bifido bacteria. Thus, they support the normal intestinal flora necessary for the function of the gastro-intestinal tract, and repress pathogenic germs; Rose, C. S., Kuhn, R., Zilliken, F. und György, P. (1954), Bifidus factor. V. the activity of α- and β-methyl-N-acetyl-D-glucosaminides, *Arch. Biochem. Biophys.* 49, 123-129.
2. Oligoraccharides prevent the adhesion of pathogenic germs and/or substances such as bacteria, toxins and eukaryotic parasites, in that they act as specific receptor analogues, the first step of an infection being thereby prevented. In various in-vitro assays, an anti-adhesive action of oligosaccharides against the most diverse pathogenic micro-organisms could be shown; Kunz, C. and Rudloff, S. (1993) Biological functions of oligosaccharides in human milk, *Acta paediatr.* 82, 903-912.
3. By influencing various immunologically active cells, oligosaccharides promote the defense against infections. The immuno-modulatory action of certain oligosaccharide structures could be shown in tests on animals by an increase of the interleukin 10 production; Velupillai, P. and Harn, D. A. (1994) Oligosaccharide-specific instruction of interleukin 10 production by B 220+ cells from schistosome-infected mice: a mechanism for regulation of CD4+ T-cell subsets, Proc. Natl. Acad. Sci. 91, 1-2.

The heterogeneity of oligosaccharides from most of the mammal milks known up to now, deviates in many respects from human milk oligosaccharides. Quantitatively, as well as qualitatively, there exist numerous differences as far as the oligosaccharide composition is concerned. The species-specific differences in the oligosaccharide content of mammal milks relate preponderantly to concentration differences of individual components, as well as to structures having similar features, and also to the basic structure itself. The monosaccharide sequence, as well as the linkage, differ as compared with the human milk oligosaccharides. In addition, the quantity of most of the individual components in most of the animal milks is significantly smaller than in the human mother's milk.

It is supposed that these differences are conditioned by the demands of the gastro-intestinal tract of the new-born baby on the oligosaccharide composition of the milk. These demands vary in a very strong manner with the different species. Such demand-contingent differences do not only vary in the comparison between a new-born child and a new-born animal, but also between various new-born animals. The differences reside in the functional condition of the gastro-intestinal tract of the new-borns, in the degree of maturity of the immune system, in the species-dependent preferred nutrition, as well as in the very specific germ medium of the respective species.

If one now tries to substitute human milk by an artificial milk or an infant formula on the basis of animal milks, then one is faced with the problem that the milk of a single animal species, according to the present state of knowledge has not the heterogeneous structural diversity with respect to the oligosaccharides, as can be found in human milk.

The object of the present invention is to provide an oligosaccharide mixture of oligosaccharides obtained from one or several animal milks, the positive activity and in particular the anti-infective activity of which corresponds to that of oligosaccharides from human milk to the largest possible extent.

This task is solved by an oligosaccharide mixture according to the teaching of the claims.

Surprisingly, it has been found that by a novel mixture of oligosaccharides from one but also from various animal milks, the anti-infective and/or prebiotic activity of the animal milk oligosaccharides is enhanced. For this reason, the inventive oligosaccharide mixture is built-up from at least two oligosaccharide fractions, with each containing at least two different oligosaccharides. The oligosaccharide fractions can thereby originate from one animal milk or also from several animal milks. Although it should be a matter of course per se, reference is made to the fact that as animal milk, human milk is not understood.

Each of the oligosaccharide fractions contains at least two different oligosaccharides. Such oligosaccharides are considered as being different, which differ with respect to at least one feature. Thus, two disaccharides, for example, which are composed of the same monosaccharide units but are differently linked, will be considered as being different oligosaccharides. The differences hence can be of a structural kind, but can also reside in the composition.

One of the essential aspects of the invention therewith resides in composing oligosaccharide fractions from animal milk of one species or of various species in a novel manner, so that an increased biological effect is achieved. Of course, it has to be secured in this new composing or mixing procedure, that there is not obtained a mixture that corresponds to the original mixture present in an animal milk or present in several animal milks. For this reason, the total spectrum of the oligosaccharides present in the oligosaccharide mixture has to differ from that of the animal milk or milks, from which the oligosaccharide fractions were obtained. When the inventive oligosaccharide mixture is, for example, obtained from only one animal milk, then it has to be expressed by the latter feature concerning the total spectrum that the new composition or mixture of the oligosaccharide fraction obtained from said single animal milk does not lead to the original animal milk again. When the oligosaccharide mixture is obtained from several animal milks, then the new composing or mixing procedure may not result in that the obtained oligosaccharide mixture corresponds to one of the oligosaccharide compositions of the originally used animal milks.

When the oligosaccharides of the inventive oligosaccharide mixture are obtained from just one animal milk, then the relationship of neutral oligosaccharides to acidic oligosaccharides is 90-60:10-40 weight %. In other words, a neutral oligosaccharide fraction is present alongside an acidic oligosaccharide fraction. Both of these fractions contain at least two different oligosaccharides. Through the modification of the ratios of the acidic oligosaccharide fraction to the neutral oligosaccharide fraction as compared to the ratios originally present in the animal milk of neutral oligosaccharides to acidic oligosaccharides, a distinctive efficiency increase can be achieved in their physiological action.

If the oligosaccharides are obtained from different and hence from at least two animal milks, a new composition or new mixture has to be carried out in such a manner that the oligosaccharides obtained from two different animal milks each amount to at least 10% by weight of the oligosaccharides present in toto in the oligosaccharide mixture. When thus the oligosaccharides are obtained from two animal milks, then the oligosaccharides obtained from one animal milk have to amount to at least 10% by weight, whereas the oligosaccharides obtained from the other animal milk likewise amount to at least 10% by weight and a maximum of 90% by weight, and vice versa. When the oligosaccharides, however, are obtained from three or more animal milks, then the oligosaccharides of only two animal milks have to amount to at least 10% by weight. The oligosaccharides from the other animal milks can amount to less than 10% by weight.

As the source for the preparation of the inventive oligosaccharide mixture, all animal milks can be used, with fractions of cow, goat, sheep, mare, camel and buffalo milk being of preferred use.

The isolation of the oligosaccharide fractions ensues with known separation methods. Thus, a fat extraction can be carried out by means of density centrifugation using a separator. A segregation of the proteins can be effected by ultrafiltration or precipitation by solvents (e.g. ethanol, acetone). Lactose can be degraded by one or several of the following methods: crystallization, filtration processes, as well as chromatographic methods (ligand exchange chromatography, gel-filtration, elution chromatography, recycling chromatography, and simulated countercurrent chromatography (SMB)). Mineral substances are separated through electrodialysis, nanofiltration, ion exchange and/or reverse osmosis. Fractionation of the oligosaccharides into neutral and acidic oligosaccharides ensues with one of the above-mentioned chromatographic methods and/or the anion exchange chromatography, as well as, alternatively, by filtration processes.

According to a preferred embodiment, the inventive oligosaccharide mixture, the oligosaccharides of which are obtained from at least two animal milks, are new composed in such a manner that in this case, as well, the ratio of neutral oligosaccharides to acidic oligosaccharides is 90-60:10-40% by weight.

With the ratio being indicated in the present documents with 90-60:10-40% by weight, at least all integral intermediate values are also covered and disclosed, e.g. 89:11, 88:12, 87:13, 85:15, 80:20, 79:21, 75:25, 74:26, 73:27, 72:28, 68:32, 67:33, 66:34, 65:35, 64: 36, 63:37, 62:38, 61:39.

The oligosaccharides of the inventive oligosaccharide mixture are preferably built-up by one or several of the following monosaccharide units: D-glucose, D-galactose, D-N-acetyl-glucosamine, D-N-acetyl galactosamine, L-fucose, D-mannose, sialic acid in the D-form (for example, D-N-acetyl neuraminic acid and D-N-glycolyl-neuraminic acid) and the O-acetylated, sulphated and phosphorylated derivatives thereof.

The free lactose present in animal milks in great amounts, for the remainder, does not count among the oligosaccharides obtained from animal milk constituting the oligosaccharide fractions used according to the invention. However, free lactose can also be present in the inventive oligosaccharide mixture, apart from the oligosaccharide fractions used according to the invention.

In other words, the inventive oligosaccharide mixture can be built-up exclusively from oligosaccharide fractions which contain oligosaccharides obtained from one or several animal milks and which are composed of two or several monosaccharide units, with free lactose not pertaining thereto. As mentioned, the oligosaccharide mixture can, however, contain free lactose, be it from animal milk or not. Moreover, the oligosaccharide mixture can contain one oligosaccharide or several oligosaccharides not originating from an animal milk. Thus, the inventive oligosaccharide mixture can, for example, be mixed with usual saccharides used for the preparation of food and in particular of infant formulae. In addition, also such oligosaccharides can be present in the inventive oligosaccharide mixture, which were released from glycolipids and/or glycoproteins during the obtainment of the inventively used oligosaccharides or oligosaccharide fractions by chemical, enzymatic and/or technological transformation.

When within the framework of the present document, it is the question of oligosaccharides, then this term refers particularly to those oligosaccharides which were obtained from animal milks. Apart from these, other oligosaccharides can likewise be present as this has been explained above, whereby this circumstance is either mentioned or results from the context.

A preferred source for the oligosaccharide isolation are milk products wherein the protein fractions, as well as the fat was removed in part and/or completely. Processing and fractionation can be significantly simplified using products such as the lactose mineral fraction resulting from the obtainment of cream, the casein fraction and the other components contained. The excess resulting from the preparation of pharmaceutical lactose likewise constitutes a suitable starter source for various oligosaccharides. Prior to carrying out the actual isolation of the fractions, the milk or lactoserum/whey of one animal species or from various animal species can thereby be mixed in the desired ratio before the oligosaccharide fractionation, such as it is necessary for the active oligosaccharide composition of single structures or structural groups.

The inventive oligosaccharide mixture can be used in a highly concentrated or a pure form in case of disorders of gastrointestinal functions in which an imbalance of bacterial species in the intestinal flora (i.e. disorder of the intestinal flora, e.g. after administration of antibiotics or other drugs influencing the intestinal flora after food intolerances, etc.) or viral infections play a role. The inventive oligosaccharide mixture can also be used for the prophylaxis against such gastro-intestinal infections. For this purpose, the inventive oligosaccharide mixture can be incorporated into an infant formula, a dietetic food or a pharmaceutical.

The inventive oligosaccharide mixture can also constitute an additive to a food complete per se. Such foods are, for example, baby foods or infant formulae and preparations for the enteric clinical nutrition. Moreover, it can be used as an additive to normal foodstuffs for conserving normal gastrointestinal functions (in the sense of a prophylaxis), as well as for the improvement of the gastro-intestinal functions after disorders wherein a faulty bacterial or a viral colonization of the gastro-intestinal tract plays a role.

The inventive oligosaccharide mixture can be conditioned as a capsule or a powder, and can be present in a diluted form as an additive to an instant food complete per se.

The inventive oligosaccharide mixture is preferably applied in an amount of at least 10 mg/kg to 4 g/kg per body weight and day, these milligram values relating to those oligosaccharides in the inventive oligosaccharide mixture which were obtained from an animal milk. The other oligosaccharides present, as the case may be, such as lactose and oligosaccharides not originating from an animal milk, thereby remain unconsidered. Particularly preferred, about 100 mg/kg are administered per body weight and day.

The invention will be explained in the following by means of the examples describing the preferred embodiments.

EXAMPLE 1

100 l of cow milk are processed according to the following method:

The fat separation is carried out by means of density centrifugation at a temperature of 45° C. The resulting fat-free milk is deproteinized by an ethanol precipitation (end concentration: 66% of ethanol). The precipitated product is separated using a separator. The ethanol and a part of the water are evaporated by means of a downflow evaporator, so as to result in a volume of 40 l. Therein, about 4 kg of lactose, 1 kg of mineral substances and other soluble components such as water-soluble vitamins, urea or citrate are contained. The portion of the oligosaccharides amounts to about 10 g. The composition of the oligosaccharide fraction consists approximately at equal parts of neutral and sialylated structures. Through anion exchange chromatography on AG 1×2, a separation into a neutral (elution means: demineralised water) and an acidic fraction (elution means: 300 mM ammonium acetate) takes place. The neutral fraction is degraded to 60% of lactose by means of the crystallization method. By means of gel chromatography on Toyopearl HW 40 (S), it is achieved that 5 g of a neutral oligosaccharide fraction are obtained, the residual lactose content of which is about 10%. The fraction of the sialylated oligosaccharides is freed from the anion exchange elution buffer (ammonium acetate) by means of electrodialysis and is freeze-dried alike the neutral oligosaccharide fraction. 4.5 g of an sialylated oligosaccharide fraction can thus be obtained. By composing anew 1 g of the acidic fraction with 5 g of the neutral fraction, a mixture of a higher activity is achieved than that corresponding to the natural composition.

EXAMPLE 2

The lactosera/wheys of goat, sheep and cow milk resulting from cheese production, are mixed in a ratio of 3:1:1 prior to being processed, so that a total lactoserum amount of 4000 l is available originating from three different animal species. By ultrafiltration with a polysulfone membrane (cutoff 20 kDa), the residual fat, the glycomacropeptide present in the solution, and the whey proteins are separated. The permeate can then be concentrated by reverse. osmosis to 900 l. The further proceeding corresponds to that described above, whereby the lactose crystallization ensues first, and subsequently the anion exchange chromatography with the target to separate peptides. The fractions of the elution stages, demineralized water and 300 mM ammonium acetate are united, concentrated, electrodialysed and freeze-dried. An oligosaccharide mixture of three different species can be obtained in an amount of 570 g. After a further separation using gel filtration and desalination by electrodialysis, the target product can be obtained by freeze-drying. The analysis with gel filtration, HPAEC and MALDI-MS shows that according to the milks used and to the mixing ratio, the ratio of acidic to neutral oligosaccharides is 1:5. The portion of the galactosyl lactoses can be indicated as being 120 g, due to the high portion of goat lactoserum. In the sheep milk, the N-glycolyl neuraminic acid prevails relative to the N-acetyl neuraminic acid as an important component of the acidic oligosaccharides. Therefore, the portion of glycolyl neuraminyl oligosaccharides is increased as compared to goat or cow milk.

EXAMPLE 3

The milks of mares and goats are processed in parallel. In each case, 50 l of milk are available. A carbohydrate-mineral matter fraction by means of centrifugation, ethanol protein precipitation and separation, is in each case obtained. Through the use of a rotary evaporator, the solutions each are fortified to 8 l. By ligand exchange chromatography on AG 501×8 ($Ca^{2+}$ form) and elution with demineralized water, the chromatographic separation of lactose and the monosaccharides, for one, and a subfractionation of the oligosaccharides, for another, takes place successfully. Between the elution range of the exclusion volume and the tetrasaccharides, a fraction from mare milk is collected, which will be used for an ulterior new composition of the oligosaccharides. The separation of the carbohydrate-mineral matter fraction from goat milk in the same phase results in a lactose-degraded and monosaccharide-degraded total oligosaccharide fraction. After a desalination and a simultaneous fortification by nanofiltration of the respective fractions, freeze-drying is carried out. The two fractions are mixed at a mixing ratio of 2:5 (mare oligosaccharide fraction:goat oligosaccharide fraction).

EXAMPLE 4

Goat milk is processed as described in Example 1. By means of anion exchange chromatography on AG 1×2, an acidic fraction is obtained, the main components thereof being 2,3'- and 2,6'-sialyl lactoses and 2,3'- and 2,6'-N-glycolyl neuraminyl lactose. This fraction is further separated by a chromatography on reversed phase material, so that a fraction results consisting of 2,3'- and 2,6'-glycolyl neuraminyl lactose. Same is desalinated by electrodialysis, spray-dried and is ready for being used for ulterior mixtures.

By means of gel filtration, the isolation of a fraction of six neutral trisaccharides from cow lactoserum takes successfully place: three isomeric galactosyl lactoses, one fucosylized lactosamine and two lactose units extended by N-acetyl galactosamine and N-acetyl glucosamine, respectively.

The acidic goat milk fraction, the prevailing structure of which constitutes the 2,3-isomer, is mixed at a ratio 1:7 with the neutral fraction of the trisaccharides from cow lactoserum in the dry state, and is ready for feeding tests.

EXAMPLE 5

The structures lacto-N-neo-tetraose and lacto-N-neo-hexaose are isolated from mare milk using the mentioned methods. These oligosaccharides are also present in human milk.

Disialyl lactose is chromatographically isolated from cow milk using the mentioned methods, and is freeze-dried.

Two position isomers of a fucosylized tetrasaccharide from goat milk are isolated using the known established methods.

The oligosaccharides are mixed in a mixing ratio of 2:1:2 (mare milk OS:cow milk OS:goat milk OS).

EXAMPLE 6

A fraction of neutral oligosaccharides can be isolated from goat lactoserum, the composition of which consists of the already described tetraoses and, moreover, pentaoses or hexaoses having a monosaccharide composition unknown up to date (2 hexosamines and 4 hexoses or 2 hexosamines and 4 hexoses, and 3 hexosamines and 3 hexoses).

From the same processing results an acidic fraction, which is fractionated by means of anion exchange chromatography in such a manner that a mixture results having a composition consisting of the two different sialyl lactoses and the two different glycolylneuraminyl lactoses. The acidic oligosaccharides having a longer chain length, as well as the neutral galactosysl lactoses, are not used for the new composition of a novel oligosaccharide mixture. The isolated acidic and the neutral fraction are mixed in the ratio 2:1.

EXAMPLE 7

Lactoserum resulting from cheese production usually contains, apart from the free oligosaccharides, also numerous bonded oligosaccharides in the form of N- and O-glycans. Thus, the glycomacropeptide is O-glycosylated, and the lactoferrin is N-glycosydated. The corresponding glycan structures are sialylated to a considerable extent. The original ratio of acidic to neutral glycans or oligosaccharides can be indicated with about 1:1. So as to shift the ratio in favor of the neutral oligosaccharides, an anion exchange chromatography is carried out. All sialylated and bonded acidic oligosaccharides (fraction 2) bond on the gel matrix, and the neutral oligosaccharides (fraction 1) are eluted with demineralized water. All charged components are eluted at a high ion strength (e.g. 1 M NaCl) and are further processed. By weak hydrolysis conditions at pH 2.0 and 45° C. for several hours, a separation of the sialic acid is achieved. After a neutralization with NaOH solution, said fraction 2 is united with the neutral oligosaccharides(fraction 1). The ratio of neutral to acidic oligosaccharides then is shifted in favor of the neutral oligosaccharides.

The invention claimed is:

1. An oligosaccharide mixture on the basis of oligosaccharides obtained from at least one animal milk and which oligosaccharides are composed of two or more monosaccharide units, wherein said oligosaccharide mixture contains:
at least two oligosaccharide fractions made up of at least two different oligosaccharides wherein,
the total spectrum of the oligosaccharides present in the oligosaccharide mixture differs from that of the animal milk or animal milks from which the oligosaccharide fractions are obtained, and that
a) if the oligosaccharides are obtained from only one animal milk, the ratio of neutral oligosaccharides to acidic oligosaccharides is 90-60:10-40% by weight, or
b) if the oligosaccharides are obtained from at least two animal milks, the oligosaccharides obtained from two different animal milks each amount to at least 10% by weight of the oligosaccharides present in toto in the oligosaccharide mixture, and the ratio of neutral oligosaccharides to acidic oligosaccharides is 90-60:10-40% by weight, with the proviso that free lactose is not included in the ratios in a) and b).

2. The oligosaccharide mixture according to claim 1, wherein the oligosaccharides are made up of at least one of the following monosaccharide units: D-glucose, D-galactose, D-N-acetyl-glucosamine, D-N-acetyl galactosamine, L-fucose, D-mannose, sialic acid in the D-form (D-N-acetyl neuraminic acid and D-N-glycolyl-neuraminic acid) and the O-acetylated, sulphated and phosphorylated derivatives thereof.

3. The oligosaccharide mixture according to claim 1, wherein the oligosaccharides were obtained from at least one of the following animal milks: cow, goat, sheep, mare, camel and buffalo milk.

4. The oligosaccharide mixture according to claim 1, wherein the oligosaccharides are obtained from unpooled or pooled milk or lactoserum or from unpooled or pooled milk products of one or several animal species.

5. The oligosaccharide mixture according to claim 1, wherein, apart from the oligosaccharides or oligosaccharide fractions, lactose is also present, which originates from the animal milk or animal milks from which the oligosaccharides are obtained, one or several oligosaccharide(s) not originating from an animal milk are present and which are present upon obtainment of the oligosaccharides by chemical, enzymatic and technological reaction of oligosaccharides released from glycoprotein and glycolipids.

6. The oligosaccharide mixture according to claim 1, wherein the said oligosaccharide mixture is incorporated into an infant formula, a dietetic food or a pharmaceutical or constitutes an additive to nutrition which is complete per se.

7. The oligosaccharide mixture according to claim 3, wherein the oligosaccharides are goat, sheep, and cow milk oligosaccharides.

8. The oligosaccharide mixture of claim 1, wherein the oligosaccharides are from at least two different animal milks each amounting to at least 10% by weight of the oligosaccharides present in toto in the oligosaccharide mixture, and the ratio of neutral oligosaccharides to acidic oligosaccharides is 90-60:10-40% by weight.

* * * * *